(12) United States Patent
Mokhasi et al.

(10) Patent No.: US 11,017,394 B2
(45) Date of Patent: May 25, 2021

(54) SYSTEM FOR VISION IMPAIRED USERS TO EXECUTE ELECTRONIC TRANSACTIONS

(71) Applicant: VISA INTERNATIONAL SERVICE ASSOCIATION, San Francisco, CA (US)

(72) Inventors: Gaurav Srikant Mokhasi, Bangalore (IN); Vyankatesh Agrawal, Bangalore (IN)

(73) Assignee: VISA INTERNATIONAL SERVICE ASSOCIATION, San Francisco, CA (US)

( * ) Notice: Subject to any disclaimer, the term of this patent is extended or adjusted under 35 U.S.C. 154(b) by 6 days.

(21) Appl. No.: 16/096,214

(22) PCT Filed: Apr. 25, 2016

(86) PCT No.: PCT/US2016/029160
§ 371 (c)(1),
(2) Date: Oct. 24, 2018

(87) PCT Pub. No.: WO2017/188924
PCT Pub. Date: Nov. 2, 2017

(65) Prior Publication Data
US 2019/0139041 A1     May 9, 2019

(51) Int. Cl.
*G06Q 20/40* (2012.01)
*G09B 21/02* (2006.01)
(Continued)

(52) U.S. Cl.
CPC .............. *G06Q 20/40* (2013.01); *A61F 9/08* (2013.01); *G06Q 20/1085* (2013.01);
(Continued)

(58) Field of Classification Search
CPC ........ G06Q 20/12; G06Q 20/02; G06Q 20/20; G06Q 20/40; G06Q 20/401; G06Q 20/385;
(Continued)

(56) References Cited

U.S. PATENT DOCUMENTS 8,205,793 B2   6/2012  Oved
8,301,564 B2  10/2012  Mon et al.
(Continued)

OTHER PUBLICATIONS

V-Braille from wayback machine, 1 page, published on Apr. 7, 2011.*
(Continued)

*Primary Examiner* — Alexander G Kalinowski
*Assistant Examiner* — Sanjeev Malhotra
(74) *Attorney, Agent, or Firm* — Loeb & Loeb, LLP

(57) ABSTRACT

A method of enabling an electronic payment for a visually impaired user may be disclosed. The visually impaired user may proceed to use the payment device and enter the braille code which may be communicated to an authority using a first channel to begin a transaction. The system may communicate a verification code to the portable computing device using a second communication channel. The user may enter the verification code which may be communicated to an authority via the first communication channel.

20 Claims, 3 Drawing Sheets

(51) Int. Cl.

| | |
|---|---|
| *G07F 19/00* | (2006.01) |
| *G07F 7/10* | (2006.01) |
| *G09B 21/00* | (2006.01) |
| *G07F 9/02* | (2006.01) |
| *G09B 21/04* | (2006.01) |
| *A61F 9/08* | (2006.01) |
| *G06Q 20/42* | (2012.01) |
| *G06Q 20/10* | (2012.01) |
| *G06Q 20/32* | (2012.01) |
| *G06Q 20/20* | (2012.01) |

(52) U.S. Cl.
CPC ............ *G06Q 20/20* (2013.01); *G06Q 20/32* (2013.01); *G06Q 20/322* (2013.01); *G06Q 20/325* (2013.01); *G06Q 20/425* (2013.01); *G07F 7/1033* (2013.01); *G07F 9/023* (2013.01); *G07F 19/201* (2013.01); *G09B 21/00* (2013.01); *G09B 21/003* (2013.01); *G09B 21/006* (2013.01); *G09B 21/02* (2013.01); *G09B 21/04* (2013.01)

(58) Field of Classification Search
CPC ...... G06Q 20/322; G06Q 20/04; G06Q 20/32; G06Q 20/3276; G06Q 20/367; G06Q 20/382; G06Q 10/10; G06Q 20/202; G06Q 20/207; G06Q 20/3674; G06Q 20/3829; G06Q 20/4014; G06Q 20/403; G06Q 20/425; G06Q 20/10; G06Q 20/18; G06Q 20/3227; G06Q 20/327; G06Q 20/3278; G06Q 20/34; G06Q 20/341; G06Q 20/36; G06Q 20/3825; G06Q 20/4016; G06Q 20/405; G06Q 20/42; G06Q 2220/00; G06Q 30/02; G06Q 30/06; G06Q 40/00; G06Q 40/02; G06Q 50/24; H04L 2209/56; H04L 2209/80; H04L 9/3213; G06F 19/328; G06F 19/3418; G06F 21/36; G06F 21/6245; G06F 19/20; G06F 19/201; G06F 7/1008; G09B 21/003; H04W 4/02
USPC ....... 705/14.1, 14.12, 16, 19, 41, 43, 44, 50, 705/64, 71, 73, 75, 76; 463/17; 340/5.54; 709/206, 229; 235/375, 380; 382/100; 434/114
See application file for complete search history.

(56) References Cited

U.S. PATENT DOCUMENTS

| | | | | |
|---|---|---|---|---|
| 2003/0041110 A1* | 2/2003 | Wenocur | ................ | H04L 63/12 709/206 |
| 2003/0074328 A1* | 4/2003 | Schiff | .................... | G07F 19/201 705/75 |
| 2004/0030607 A1* | 2/2004 | Gibson | ................ | G06Q 20/085 705/75 |
| 2008/0257959 A1* | 10/2008 | Oved | .................... | G06Q 20/401 235/380 |
| 2009/0164326 A1* | 6/2009 | Bishop | ................... | G06Q 20/20 705/19 |
| 2009/0164327 A1* | 6/2009 | Bishop | ................... | G06Q 20/12 705/19 |
| 2009/0164330 A1* | 6/2009 | Bishop | ................. | G06Q 20/202 705/19 |
| 2009/0284344 A1* | 11/2009 | Craymer | .................. | G07C 9/33 340/5.54 |
| 2009/0287837 A1* | 11/2009 | Felsher | ................. | G06Q 10/10 709/229 |
| 2010/0257065 A1 | 10/2010 | Gupta | | |
| 2010/0312703 A1* | 12/2010 | Kulpati | ................ | G06Q 20/322 705/44 |
| 2011/0184865 A1* | 7/2011 | Mon | ....................... | G07F 19/20 705/43 |
| 2011/0281630 A1* | 11/2011 | Omar | .................... | H04L 63/105 463/17 |
| 2012/0114169 A1* | 5/2012 | Hannigan | ............ | G06Q 10/087 382/100 |
| 2012/0271768 A1* | 10/2012 | Kang | ................... | G06Q 20/425 705/44 |
| 2012/0315606 A1* | 12/2012 | Jwa | ...................... | G09B 21/003 434/114 |
| 2013/0185214 A1* | 7/2013 | Azen | .................. | G06Q 20/3272 705/76 |
| 2013/0193201 A1* | 8/2013 | Bradley | ............. | G06Q 30/0623 235/375 |
| 2013/0211933 A1* | 8/2013 | Yoo | ....................... | G06Q 20/322 705/16 |
| 2013/0325567 A1* | 12/2013 | Bradley | ............. | G06Q 30/0207 705/14.1 |
| 2014/0058812 A1* | 2/2014 | Bender | ............. | G06Q 30/0209 705/14.12 |
| 2014/0156510 A1 | 6/2014 | Howe | | |
| 2014/0222684 A1* | 8/2014 | Felsher | .................. | G16H 10/60 705/50 |
| 2014/0236834 A1* | 8/2014 | Appalsamy | .......... | G06Q 20/387 705/64 |
| 2014/0351146 A1* | 11/2014 | Johnson | ................. | G06Q 30/02 705/71 |
| 2014/0365373 A1* | 12/2014 | Pelegero | ............ | G06Q 20/3223 705/44 |
| 2015/0149360 A1 | 5/2015 | Ezequiel | | |
| 2015/0220925 A1* | 8/2015 | Brickell | ................ | G06Q 20/36 705/41 |
| 2016/0012400 A1* | 1/2016 | McCarthy | .............. | G06Q 20/12 705/73 |
| 2016/0012430 A1* | 1/2016 | Chandrasekaran | .. | G06Q 20/405 705/44 |
| 2016/0358180 A1* | 12/2016 | Van Os | ................. | G06Q 20/321 |
| 2017/0083909 A1* | 3/2017 | Mork | .................... | G06Q 20/401 |
| 2017/0116588 A1* | 4/2017 | Conant | ............. | G06Q 20/3552 |
| 2017/0193855 A1* | 7/2017 | Yang | .................... | G09B 21/004 |
| 2017/0215032 A1* | 7/2017 | Horbal | .................... | H04W 4/02 |
| 2017/0300918 A1* | 10/2017 | Bernstein | ............. | G06Q 20/385 |
| 2018/0006821 A1* | 1/2018 | Kinagi | ................... | H04L 9/3234 |
| 2018/0047010 A1* | 2/2018 | Itwaru | ................. | G06Q 20/322 |
| 2018/0275811 A1* | 9/2018 | Filiz | .................... | G06F 3/04166 |
| 2018/0365692 A1* | 12/2018 | Kortina | ................ | G06Q 20/227 |
| 2019/0272529 A1* | 9/2019 | Itwaru | .................... | G06Q 20/42 |

OTHER PUBLICATIONS

Extended European Search Report for Application No. EP16900668.1, dated Oct. 15, 2019, 9 pages.

International Searching Authority, "International Search Report and Written Opinion," issued in connection with application No. PCT/US16/29160, dated Jul. 29, 2016, 11 pages.

* cited by examiner

SYSTEM FOR VISION IMPAIRED USERS TO EXECUTE ELECTRONIC TRANSACTIONS

CROSS-REFERENCE TO RELATED APPLICATIONS

This application claims priority under 35 U.S.C. 371 to PCT/US2016/029160 filed Apr. 25, 2016, entitled "System For Vision Impaired Users To Execute Electronic Transactions" the entire disclosure of which is expressly incorporated by reference herein.

BACKGROUND

The visually impaired have challenges using modern electronic devices. Technology makes transactions easier for many people, but the visually impaired have difficulty taking full advantage of the new technology. Some devices have been created to make input easier such electronic braille devices which may allow a visually impaired person to use some functionality of modern electronic devices.

SUMMARY

The following presents a simplified summary of the present disclosure in order to provide a basic understanding of some aspects of the disclosure. This summary is not an extensive overview. It is not intended to identify key or critical elements of the disclosure or to delineate its scope. The following summary merely presents some concepts in a simplified form as a prelude to the more detailed description provided below.

In one embodiment, a visually impaired user may register a payment device with an indication that the user is visually impaired. The system may assign a braille code to the payment device and a portable computing device of the user. The user may then proceed to use the payment device and enter the braille code which may be communicated to an authority using a first channel to begin a transaction. The system may communicate a verification code to the portable computing device using a second communication channel. The user may enter the verification code which may be communicated to an authority via the first communication channel. In response to the verification code, braille code and computing device being recognized, the transaction may be authorized.

BRIEF DESCRIPTION OF THE DRAWINGS

The invention may be better understood by references to the detailed description when considered in connection with the accompanying drawings. The components in the figures are not necessarily to scale, emphasis instead being placed upon illustrating the principles of the invention. In the figures, like reference numerals designate corresponding parts throughout the different views.

Persons of ordinary skill in the art will appreciate that elements in the figures are illustrated for simplicity and clarity so not all connections and options have been shown to avoid obscuring the inventive aspects. For example, common but well-understood elements that are useful or necessary in a commercially feasible embodiment are not often depicted in order to facilitate a less obstructed view of these various embodiments of the present disclosure. It will be further appreciated that certain actions and/or steps may be described or depicted in a particular order of occurrence while those skilled in the art will understand that such specificity with respect to sequence is not actually required. It will also be understood that the terms and expressions used herein are to be defined with respect to their corresponding respective areas of inquiry and study except where specific meanings have otherwise been set forth herein.

SPECIFICATION

The present invention now will be described more fully with reference to the accompanying drawings, which form a part hereof, and which show, by way of illustration, specific exemplary embodiments by which the invention may be practiced. These illustrations and exemplary embodiments are presented with the understanding that the present disclosure is an exemplification of the principles of one or more inventions and is not intended to limit any one of the inventions to the embodiments illustrated. The invention may be embodied in many different forms and should not be construed as limited to the embodiments set forth herein; rather, these embodiments are provided so that this disclosure will be thorough and complete, and will fully convey the scope of the invention to those skilled in the art. Among other things, the present invention may be embodied as methods, systems, computer readable media, apparatuses, or devices. Accordingly, the present invention may take the form of an entirely hardware embodiment, an entirely software embodiment, or an embodiment combining software and hardware aspects. The following detailed description is, therefore, not to be taken in a limiting sense.

Figure 1:
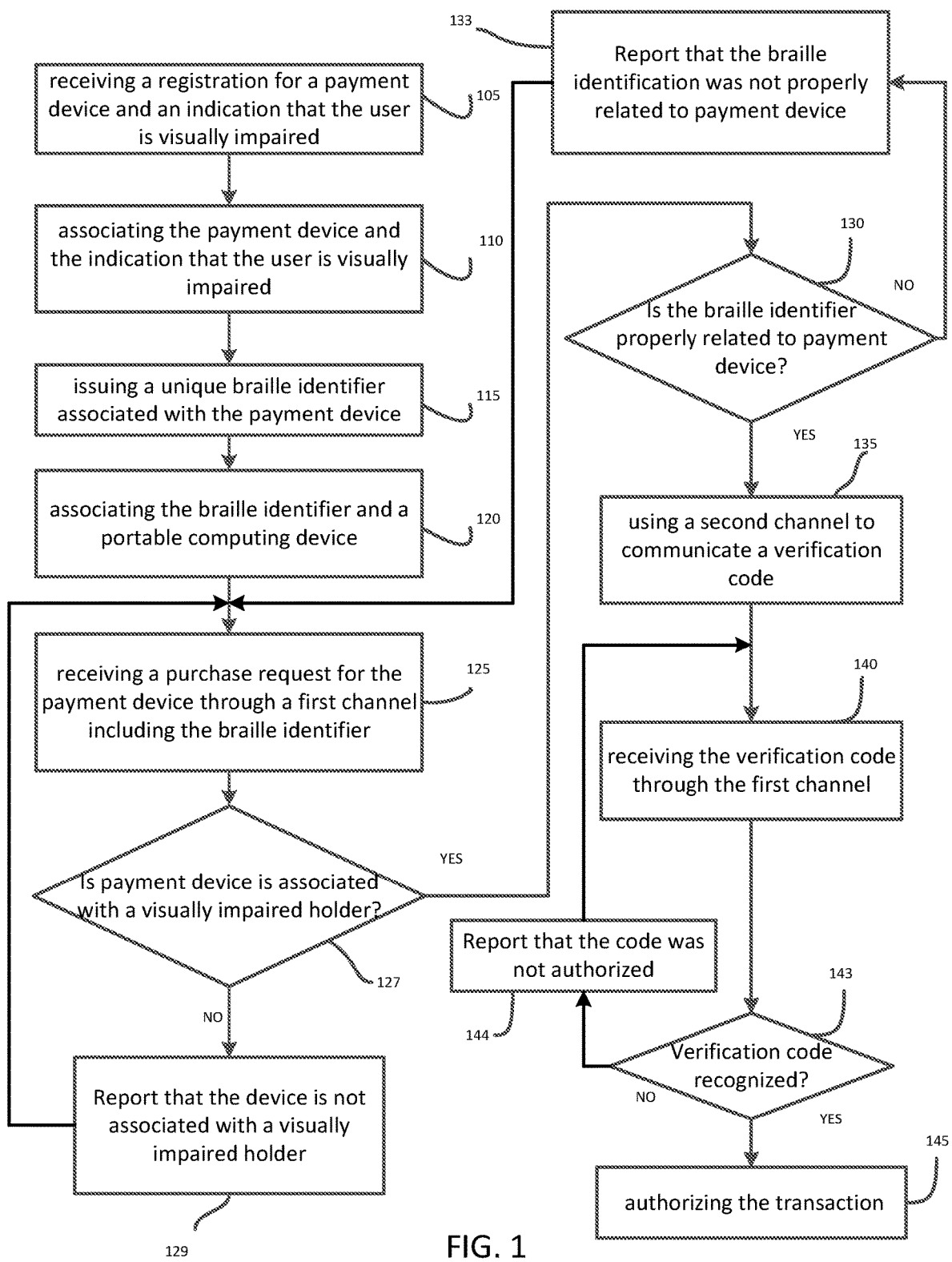
FIG. 1 is an illustration of a method of providing electronic services to a visually impaired person.

Referring to FIG. 1, computer instructions may physically configure a processor to execute block of computer instruction for a method of enabling an electronic payment for a visually impaired user. Making secure payments for vision impaired individuals may be a technical problem that requires a technical solution. For example, a tradition point of sale terminal is very hard for the visually impaired to use. Similarly, modern payment applications like Visa Checkout make it hard for users to navigate the many visual choices necessary to complete a transaction. The described system and method uses inventive hardware and inventive software to create a technical solution to allow the visually impaired to use a variety of payment devices anywhere at any time.

At block 105, a registration for a payment device and an indication that the user is visually impaired may be received by an authority. In one embodiment, a user may register a debit card using a computer with a card issuer web site. In another embodiment, the payment device may be an account number for a bank account. In yet another embodiment, the payment device may be a payment application that operates on a portable computing device such as a smart phone and the payment application may have access to several payment accounts that may be used by the payment application.

The authority may take on a variety of forms. In some embodiments, the authority may be a card issuing bank. In another embodiment, the authority may be a payment clearance center. In another embodiment, a separate authority may be created to handle transaction for the visually impaired. The hardware may include a registration sever such as the server 240 in FIG. 3 that is physically configured to receive and process registrations.

At block 110, the payment device may be associated with the indication that the user is visually impaired in a memory which may be part of the payment processing system. The indication may be used to accept different data than a traditional transaction. Further, the indication may be used to route messages about the payment device to a computing device that is capable of receiving and processing a transaction for a payment device for the visually impaired.

At block 115, a unique braille identifier associated with the payment device may be issued by the authority. The braille identifier may be a code which the user enters on a braille enabled input device 335 on the portable computing device or into a computing device. The identifier may be stored in a memory that is accessible to the authority such that future transactions may use the identifier as a verification. The braille identifier may be identifier that is designed to be easy to input on a braille input device 335 but may be difficult to guess. In one embodiment, the identifier is six digits but, of course, the identifier could be alpha, a combination of alpha and numerical and could have a variety of lengths. The braille identifier may be generated by a braille identifier server such as a version of the server 240 in FIG. 3 which is specifically built to generate braille identifiers.

At block 120, the authority may associate the braille identifier and a portable computing device. In one embodiment, the authority may have a database with portable computing device identifiers and braille identifiers stored in a memory. In addition, the payment account may also be associated with in the same database with the portable computing device and the identification code.

At block 125, a purchase request may be received for the payment device through a first channel including the braille identifier. As an example, a visually impaired user may make a purchase at a store using a debit card. Using the portable computing device, the user may enter the braille identifier which may be communicated to the authority. The identification code may be entered into a braille input screen on the portable computing device. In another embodiment, the point of sale device at the store may have a braille input device 335 and the user may enter the braille identification code into the braille input device 335 connected to the point of sale device. In some embodiments, the portable computing device may communicate wirelessly to the point of sale device. In other embodiments, the portable computing device may communicate wirelessly through a network to the authority. The purchase request may be communicated to a purchase request server such as a version of the server 240 in FIG. 3 which may be specifically built to receive and analyze purchase requests.

At block 127, it may be determined if the payment device is associated with a visually impaired holder. If the payment device is not associated with a visually impaired holder, the method may, at block 129, report that the device is not associated with a visually impaired holder and the method may return to block 125.

At block 130, in response to the authority recognizing that the payment device is associated with a visually impaired holder, the method may determine if the braille identifier from the portable computing device is properly related to payment device. In one embodiment, the payment device and received braille identifier will be compared to those in the memory accessible to the authority that has been stored as being related. As an example, the authority make looked up whether Ralph's phone is associated with the received braille code 123456. If there is a match, the method may proceed. If there is not a match, the system may indicate the braille code did not match a payment device stored in the memory.

If the braille identifier is not properly related to a payment device, control may pass to block 133 where it may be reported that the braille identification was not properly related to a payment device. Thereafter, control may pass to block 125 where the user my try again.

At block 135, in response to the braille identifier being recognized from the portable computing device, a second channel may be used to communicate a verification code. In one embodiment, the second channel may be a second wireless communication channel and the first wireless communication channel is different than the second wireless communication channel. The second communication channel carries voice data and the verification code may be communicated via a voice to the user. In some embodiments, a communication server is user which is physically created to communicate verification codes to the visually impaired which may be different than other traditional communications.

At block 140, the verification code may be received through the first channel. In one embodiment, the user may type in the received verification code into the braille input device 335. The braille input device 335 may be in communication with a portable computing device, with the point of sale or may be free standing. The verification code may be communicated wirelessly to the authority, in some embodiments through a point of sale device and in other embodiments, through a network which may be in communication with the authority. In some embodiments, the verification code may be carried over the payment network to the authority. A payment network is a separate, secure network used to carry payment data traffic.

At block 143, the verification code may be tested to see if the verification code if recognized as the code that was sent to the user. The verification code may be tested by a verification server which may be specifically created to test verification codes, including verification codes from the visually impaired which may be distinct from traditional verification methods. If the verification code is not recognized, control may pass to block 144 where it may be reported that the braille identification was not properly related to a payment device. Thereafter, control may pass to block 140 where the user my try again.

At block 145, in response to the verification code being recognized, the transaction may be authorized. In operation, the authority has used a second channel to communicate a verification code via a phone call to a visually impaired user which the user enters using a braille input to verify the transaction. In some embodiments, the authorization may be communicated to the user. The authorization may be completed using an authorization server which is specifically built to determine authorizations, including authorizations for the visually impaired.

Figure 2:
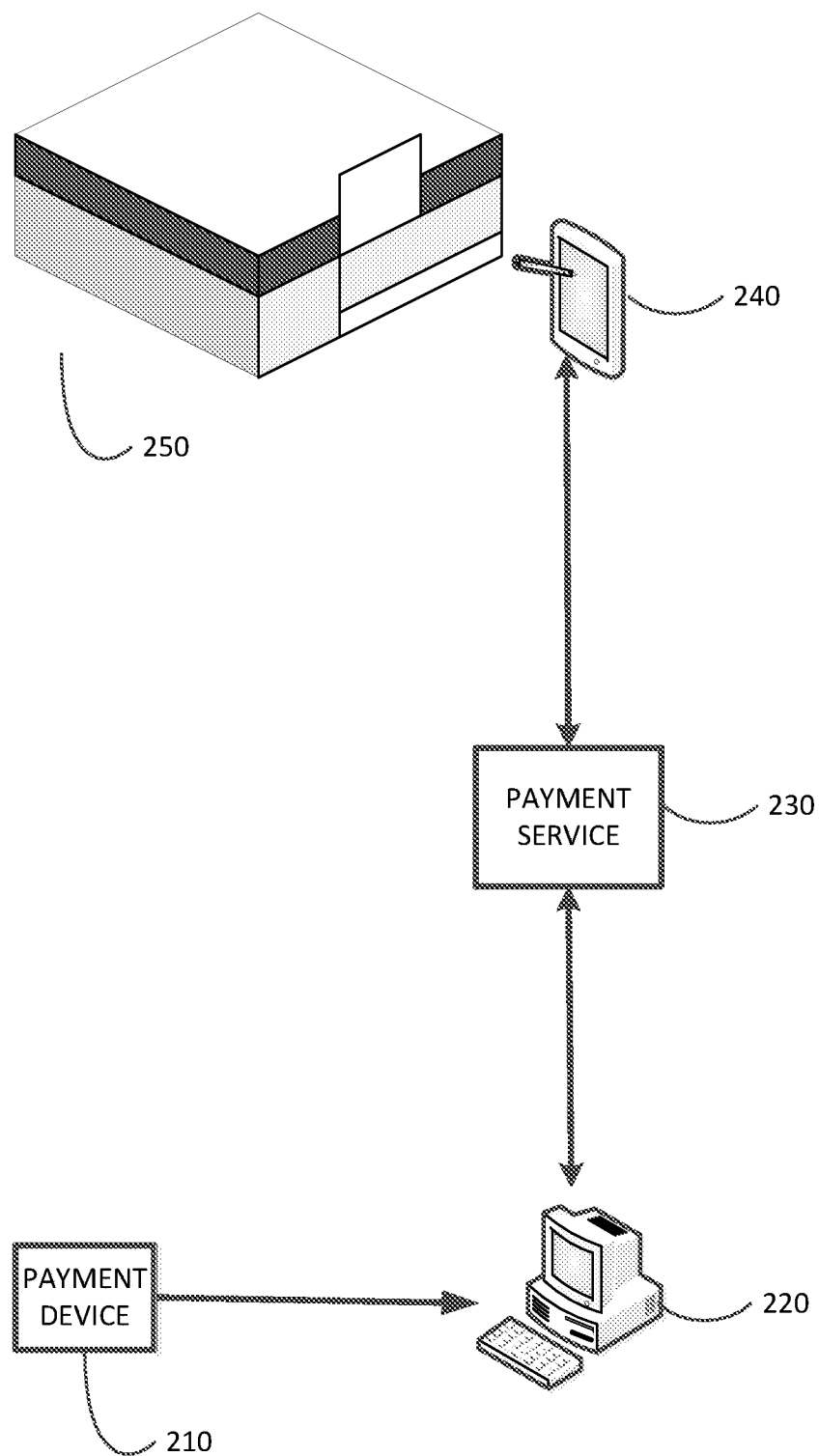
FIG. 2 is an illustration the hardware that is part of the system.

FIG. 2 may further illustrate a sample transaction that uses the method. A user may register a payment device 210 using a computing device 220 with the authority 230. The payment device 210 and a portable computing device 240 of the user may be associated in a memory of the authority 230. The user may then proceed to a store 250, open up a payment application on the portable computing device 240 and may begin a transaction. The portable computing device identification and braille code may be communicated to the authority on a first channel such as a payment network or via the Internet. If the portable computing device identification and braille code match an entry in the memory available to the authority 230, the authority 230 may use a second channel to communicate a verification code to the computing device 240 associated with the transaction. The user may then enter the verification code into portable computing device which may be communicated to the authority 230 wirelessly, or through a payment network or through the Internet in general. If the verification code is recognized, the transaction may be approved by the authority and the approval may be communicated to the user via the portable computing device 240.

Figure 3:
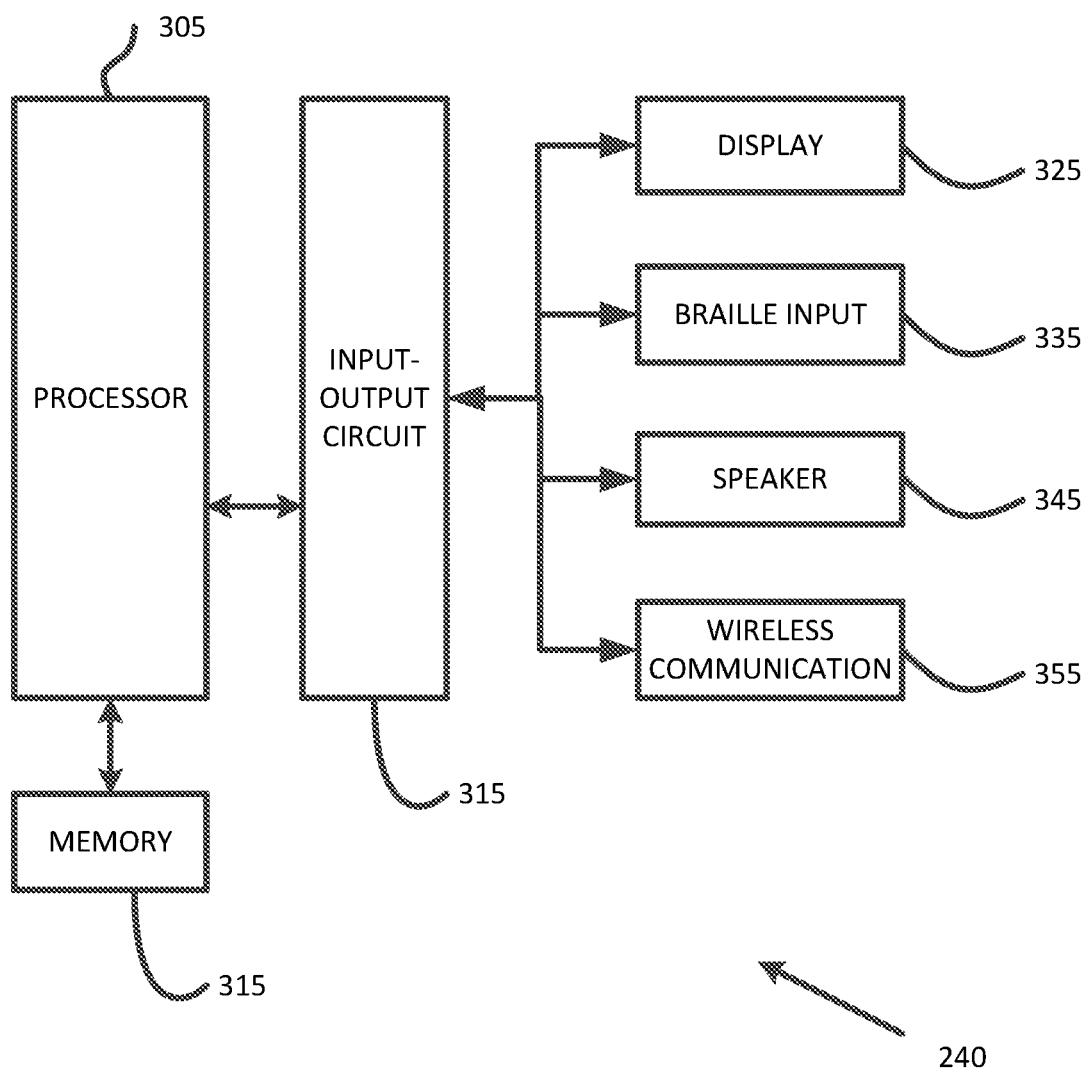
FIG. 3 is an illustration of the hardware in the portable computing device that is used as part of the system.

FIG. 3 may illustrate the physical elements that may be used by the portable computing device 240. The portable computing device 240 may have a processor 305 which may be physically configured according to computer executable instructions. A memory 315 may be in communication with the processor 305 and the memory may store the portable computing device ids, the braille codes, the verification codes and other data that may be useful to the processor 305. The processor 305 may be in communication with an input-output circuit 315 which may manage communications to and from the processor 305. The input-output circuit 315 may be in communication with a display 325 which may be touch sensitive and may be optimized for the visually impaired. The input-output circuit 315 may be in communication with a braille input device 335 which may use electronics to physically form numbers and letters which can be understood by touch by the visually impaired. The input-output circuit 315 may be in communication with a speaker 345 which may be used to communicate messages to the user by voice. The input-output circuit 315 may be in communication with a wireless communication circuit which may be used to communicate wirelessly in a variety of forms such as via Bluetooth, WiFi, cellular, or any other appropriate RF communication form and format.

The user devices, computers and servers described herein may have, among other elements, a microprocessor (such as from the Intel Corporation, AMD or Motorola); volatile and non-volatile memory; one or more mass storage devices (i.e., a hard drive); various user input devices, such as a mouse, a keyboard, or a microphone; and a video display system. The user devices, computers and servers described herein may be running on any one of many operating systems including, but not limited to WINDOWS, UNIX, LINUX, MAC OS, or Windows (XP, VISTA, etc.). It is contemplated, however, that any suitable operating system may be used for the present invention. The servers may be a cluster of web servers, which may each be LINUX based and supported by a load balancer that decides which of the cluster of web servers should process a request based upon the current request-load of the available server(s).

The user devices, computers and servers described herein may communicate via networks, including the Internet, WAN, LAN, Wi-Fi, other computer networks (now known or invented in the future), and/or any combination of the foregoing. It should be understood by those of ordinary skill in the art having the present specification, drawings, and claims before them that networks may connect the various components over any combination of wired and wireless conduits, including copper, fiber optic, microwaves, and other forms of radio frequency, electrical and/or optical communication techniques. It should also be understood that any network may be connected to any other network in a different manner. The interconnections between computers and servers in system are examples. Any device described herein may communicate with any other device via one or more networks.

The example embodiments may include additional devices and networks beyond those shown. Further, the functionality described as being performed by one device may be distributed and performed by two or more devices. Multiple devices may also be combined into a single device, which may perform the functionality of the combined devices.

The various participants and elements described herein may operate one or more computer apparatuses to facilitate the functions described herein. Any of the elements in the above-described Figures, including any servers, user devices, or databases, may use any suitable number of subsystems to facilitate the functions described herein.

Any of the software components or functions described in this application, may be implemented as software code or computer readable instructions that may be executed by at least one processor using any suitable computer language such as, for example, Java, C++, or Perl using, for example, conventional or object-oriented techniques.

The software code may be stored as a series of instructions or commands on a non-transitory computer readable medium, such as a random access memory (RAM), a read only memory (ROM), a magnetic medium such as a hard-drive or a floppy disk, or an optical medium such as a CD-ROM. Any such computer readable medium may reside on or within a single computational apparatus and may be present on or within different computational apparatuses within a system or network.

It may be understood that the present invention as described above can be implemented in the form of control logic using computer software in a modular or integrated manner. Based on the disclosure and teachings provided herein, a person of ordinary skill in the art may know and appreciate other ways and/or methods to implement the present invention using hardware, software, or a combination of hardware and software.

The above description is illustrative and is not restrictive. Many variations of the invention will become apparent to those skilled in the art upon review of the disclosure. The scope of the invention should, therefore, be determined not with reference to the above description, but instead should be determined with reference to the pending claims along with their full scope or equivalents.

One or more features from any embodiment may be combined with one or more features of any other embodiment without departing from the scope of the invention. A recitation of "a", "an" or "the" is intended to mean "one or more" unless specifically indicated to the contrary. Recitation of "and/or" is intended to represent the most inclusive sense of the term unless specifically indicated to the contrary.

One or more of the elements of the present system may be claimed as means for accomplishing a particular function. Where such means-plus-function elements are used to describe certain elements of a claimed system it will be understood by those of ordinary skill in the art having the present specification, figures and claims before them, that the corresponding structure is a general purpose computer, processor, or microprocessor (as the case may be) programmed to perform the particularly recited function using functionality found in any general purpose computer without special programming and/or by implementing one or more algorithms to achieve the recited functionality. As would be understood by those of ordinary skill in the art that algorithm may be expressed within this disclosure as a mathematical formula, a flow chart, a narrative, and/or in any other manner that provides sufficient structure for those of ordinary skill in the art to implement the recited process and its equivalents.

While the present disclosure may be embodied in many different forms, the drawings and discussion are presented with the understanding that the present disclosure is an exemplification of the principles of one or more inventions and is not intended to limit any one of the inventions to the embodiments illustrated.

The present disclosure provides a solution to the long-felt need described above. In particular, the systems and methods described herein may be configured for improving payment systems. Further advantages and modifications of the above described system and method will readily occur to those skilled in the art. The disclosure, in its broader aspects, is therefore not limited to the specific details, representative system and methods, and illustrative examples shown and described above. Various modifications and variations can be made to the above specification without departing from the scope or spirit of the present disclosure, and it is intended that the present disclosure covers all such modifications and variations provided they come within the scope of the following claims and their equivalents.

The invention claimed is:

1. A computer-implemented method of enabling an electronic payment for a visually impaired user comprising:
   receiving a registration for a payment device and an indication that the visually impaired user corresponds to the payment device;
   associating the payment device and the indication;
   issuing a unique braille identifier associated with the payment device;
   associating the braille identifier and a portable computing device, wherein the portable computing device corresponds to the visually impaired user and includes a braille input device having a braille input screen to receive the braille identifier;
   receiving a purchase request for the payment device through a first channel at a purchase request server, the purchase request initiated at a point of sale device at a store computer system, the purchase request including the braille identifier;
   automatically sending a first control signal to the braille input device of the portable computing device that is communicably connected to the point of sale device, wherein the first control signal configures the portable computing device to display the braille input screen to receive the braille identifier in response to the first channel at the purchase request server receiving the purchase request;
   determining if the braille identifier received at the portable computing device is properly related to the payment device;
   in response to the braille identifier being recognized from the portable computing device, automatically sending a second control signal to the portable computing device for initiating a phone call using a second channel to communicate a verification code to the portable computing device;
   in response to the second control signal, receiving the verification code at an authority server from the portable computing device through the first channel; and
   in response to the verification code being recognized, communicating an authorization for the transaction from the authority server.

2. The method of claim 1, wherein the braille identifier is further associated with a portable computing device at a payment processor.

3. The method of claim 1, wherein the payment device provides access to an account that is payment capable.

4. The method of claim 1, wherein the braille identifier comprises a code which the user enters on a braille enabled input device.

5. The method of claim 1, wherein the first channel comprises a first wireless communication channel.

6. The method of claim 1, wherein the second channel comprises a second wireless communication channel and the first wireless communication channel is different than the second wireless communication channel.

7. The method of claim 6, wherein the second communication channel carries voice data.

8. The method of claim 7, wherein the verification code is communicated via a voice to the user.

9. The method of claim 8, wherein the user enters the verification code via an input device on a portable computing device.

10. The method of claim 9, wherein the verification code is communicated wirelessly to an authority.

11. The method of claim 9, wherein the verification code is communicated to a point of sale device.

12. The method of claim 9, wherein the verification code is communicated to the authority over a payment network.

13. The method of claim 1, further comprising communicating the authorization to the user.

14. The method of claim 11, further comprising utilizing a payment application operating on the portable computing device.

15. The method of claim 1, further comprising registering the debit card using a braille accessible computer over a payment network.

16. A processor-implemented system for enabling an electronic payment for a visually impaired user comprising:
   an authority server including a processor and a memory disposed in communication with the memory and storing processor-executable instructions for:
      receiving a registration for a payment device and an indication that the visually impaired user corresponds to the payment device;
      associating the payment device and the indication;
      issuing a unique braille identifier associated with the payment device;
      associating the braille identifier and a portable computing device, wherein the portable computing device corresponds to the visually impaired user and includes a braille input device having a braille input screen to receive the braille identifier;
      receiving a purchase request for the payment device through a first channel at a purchase request server, the purchase request initiated at a point of sale device at a store computer system, the purchase request including the braille identifier;
      automatically sending a first control signal to the braille input device of the portable computing device that is communicably connected to a point of sale device, wherein the first control signal configures the portable computing device to display the braille input screen to receive the braille identifier in response to the first channel at the purchase request server receiving the purchase request;
      determining if the braille identifier received at the portable computing device is properly related to the payment device;
      in response to the braille identifier being recognized from the portable computing device, automatically sending a second control signal to the portable computing device for initiating a phone call using a second channel to communicate a verification code to the portable computing device;

in response to the second control signal, receiving the verification code at the authority server from the portable computing device through the first channel; and in response to the verification code being recognized, communicating an authorization for the transaction from the authority server.

17. The system of claim 16, wherein the braille identifier is further associated with a portable computing device at a payment processor.

18. The system of claim 16, wherein the first channel comprises a first wireless communication channel, the second channel comprises a second wireless communication channel, the first wireless communication channel is different than the second wireless communication channel, and the second communication channel carries voice data.

19. The system of claim 16, further comprising communicating the authorization to the user utilizing a payment application operating on the portable computing device.

20. The system of claim 16, wherein the debit card is registered using a braille accessible computer over a payment network.

* * * * *